United States Patent [19]

Lardner et al.

[11] Patent Number: 4,754,895

[45] Date of Patent: Jul. 5, 1988

[54] DRAIN CLOSURE

[75] Inventors: George E. Lardner, Seminole; Jacek Weinheimer, Treasure Island, both of Fla.

[73] Assignee: Halkey-Roberts Corporation, St. Petersburg, Fla.

[21] Appl. No.: 868,644

[22] Filed: May 29, 1986

[51] Int. Cl.$^4$ ............................................. B65D 41/04
[52] U.S. Cl. ..................................... 220/288; 220/375
[58] Field of Search ............... 220/288, DIG. 19, 375; 383/66, 59, 96; 215/356; 604/256

[56] References Cited

U.S. PATENT DOCUMENTS

| | | | |
|---|---|---|---|
| 2,777,490 | 1/1957 | Munk | 383/66 |
| 4,542,530 | 9/1985 | Thomas et al. | 383/66 |

*Primary Examiner*—George T. Hall
*Attorney, Agent, or Firm*—Dominik, Stein, Saccocio & Reese

[57] ABSTRACT

A drain closure valve is disclosed having a wide mouth body member including a substantially cylindrical body annular wall portion with a fluid passageway therethrough and having a cap for sealing engagement therewith. The cap includes a substantially cylindrical cap annular wall portion and a bottom wall portion, a stepped annular ridge which defines a ridge upper annular wall portion and a ridge lower annular wall portion joined by a ridged upper horizontal wall portion, and threads affixed to the annular wall portions of the cap and the body member allowing the cap to threadably engage the body member. The seal comprises a protrusion extending outwardly from the cap annular wall portion which sealingly engages against the lumen of the body annular wall portion.

12 Claims, 1 Drawing Sheet

DRAIN CLOSURE

BACKGROUND OF THE INVENTION

1. Field of the Invention

This invention relates to drain closures for filling and draining a container such as a flexible plastic bag. More particularly, this invention relates to drain closures having a removable cap sealingly engaged within a body member.

2. Description of the Background Art

Presently, there exist numerous types of valves operable to allow the filling and drainng of a container. Specific types of valves have been developed for use in conjunction with a bladded type container composed of thin walled plastic. For example, in the medical fields, several valves have been developed for allowing the filling and draining of plastic bag-type containers such as intravenous bags, urinary collection bags, and enema bags. U.S. Pat. No. 3,177,871 discloses one such bag consisting of a disposable sanitary container for radiographic enemas. Obviously, the need for drain closure valves of this character is widespread and not limited to the various medical fields.

U.S. Pat. No. 2,777,490, the disclosure which is hereby incorporated by reference herein discloses one such valve which is particulariy adaptable for use in conjunction with bag-type containers. This valve comprises a body member having an annular cylindrical wall which is adhered to the plastic sheeting or wall of the bag by a radio frequency (RF) sealing or the like. A removable plug is provided for sealingly engaging into the axial hole extending through the body member to tightly seal and, hence, close the valve. Notably, the plug and, correspondingly, the axial hole extending through the body member comprise a large diameter to allow rapid filling and draining of the bag-type container. The wide mouth of the drain closure valve also minimizes the inadvertent spilling of the fluid as it is poured into the container to fill the same.

The aforementioped drain closure valve has been widely accepted throughout the industry, particularly in the medical fields. Unfortunately, a major drawback to the drain closure valve of such design is the difficulty in removing the plug from the body member to allow filling of the container. Specifically, due to the wide mouth of the body member and the resulting side width of the plug, a significant force must be exerted on the plug to disengage its sealing engagement with the body member. Further, since the plug releases quickly when sufficient force is exerted, the body member and the plug are jarred or jerked to such a degree (in the hands of the operator) that the fluid contained in the container tends to spill onto the outside of the container. Obviously, such spillage during the opening of the drain closure valve occurs more frequently depending on the level of fluid in the container in relation to the wide mouth of the drain closure valve. Thus, there exist is a need for a drain closure valve which can be conveniently opened without jarring or jerking the container thereby preventing spillage of the fluid from the container, without reducing the ability of the plug or cap to seal within the body member when closed.

Therefore, it in an object of this invention to provide an apparatus which overcomes the aforementioned inadequacies of the prior art devices and provides an improvement which is a significant contribution to the advancement of the drain closure art.

Another object of this invention is to provide a drain closure valve having a plug or cap which sealingly engages into a body member to form an airtight seal therewith preventing leakage of a fluid through the axial opening of the body member.

Another object of this invention is to provide a drain closure valve having a capped body member capable of being sealed to the thin wall of a container such as a bag-type container composed of thin walled plastic sheeting or the like.

Another object of this invention is to provide a drain closure valve having a capped body member having a wide mouth opening therethrough, allowing quick filling and draining of the container during use.

Another object of this invention is to provide a capped drain closure valve comprising a cap which threadably and sealingly engages a body member to form an airtight seal therewith in such a manner that the cap may be removed from the body member without excessive force which may otherwise result in jerking or jarring of the drain closure valve and the container thereby minmizing spillage of the fluid from the container during opening.

Another object of this invention is to provide a capped drain closure valve which may be economically manufactured by injection molding techniques to render the drain closure valve "disposable" after use.

The foregoing has outlined some of the more pertinent objects of the invention. These objects should be construed to be merely illustrative of some of the more prominent features and applications of the intended invention. Many other beneficial results can be obtained by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a drain closure valve comprising a cap which threadably and sealingly engages a substantially cylindrical body member to form an airtight seal therewith. More particularly, the drain closure valve of the invention comprises an upward cylindrical wall member and a lower cylindrical wall member of a reduced diameter joined together at a lowerly converging frustro-conical wall member, thereby defining a widemouth axial opening therethrough. The lower annular wall portion of the body member is designed to be welded to the plastic sheeting of a bag-type container or the like using conventional RF welding techniques.

The drain closure valve of the invention further comprises a substantially cylindrical cap for sealing engagement with the upper annular wall portion of the body member by means of specially configured threads formed on the lower outer surface of the cap and the lumen of the upward annular wall portion of the body member. Further, the cap sealingly engages the upper annular wall portion of the body member by means of an interlocking seal formed therebetween as the cap is threaded into the body member.

An important feature of the invention is the interlocking seal formed between the cap and the body member which actually begins forming the seal therebetween as the cap is threaded into the body member. Formation of the seal between the cap and the body member before the cap is tightly threaded into the body member precludes spillage of the fluid from the container as the cap is tightened. Moreover, during opening, the seal formed between the cap and the body member is maintained until the cap is released from its tightened threaded position in the body member. Thus, even though jerking of the drain closure valve and the container during opening is minimized because of the threaded engagement of the cap with the body member, any jerking which may nevertheless occure does not result in spillage of the fluid from the container since he seal between the cap and the body member is maintained as the cap is loosened from the body member. Consequently, spillage of the fluid during opening is precluded irrespective of how tight the cap may have been threaded into the body member.

The foregoing has outlined rather broadly the more pertinent and important features of the present invention in order that the detailed discription of the invention that follows may be better understood so that the present contribution to the art can be more fully appreciated. Additional features of the invention will be described hereinafter which form the subject of the claims on the invention. It should be appreciated by those skilled in the art that the conception and the specific embodiment disclosed may be readily utilized an a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
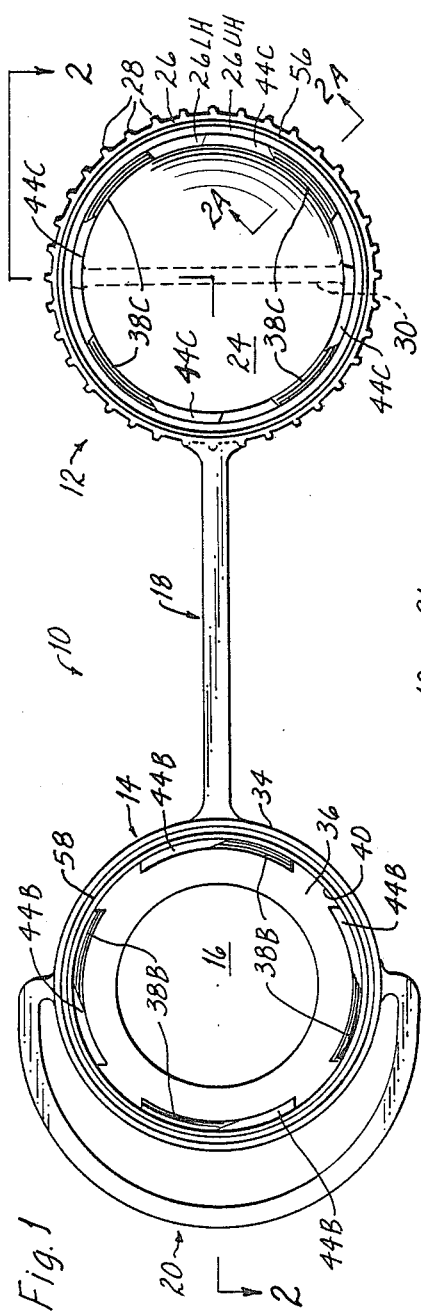
FIG. 1 is a top view of the drain closure valve of the invention in its opened position with the cap thereof being tethered to the body member thereof.
Figure 2A:
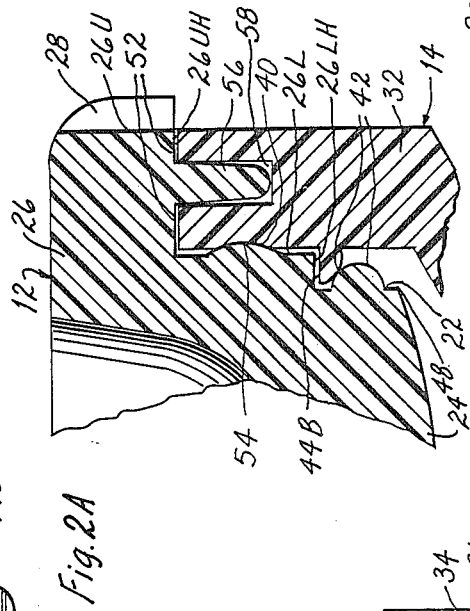
FIG. 2A is an enlarged partial cross sectional view of FIG. 1 along lines 2—2 illustrating the sealing engagement of the cap with the body member of the drain closure in the closed position.
Figure 2:
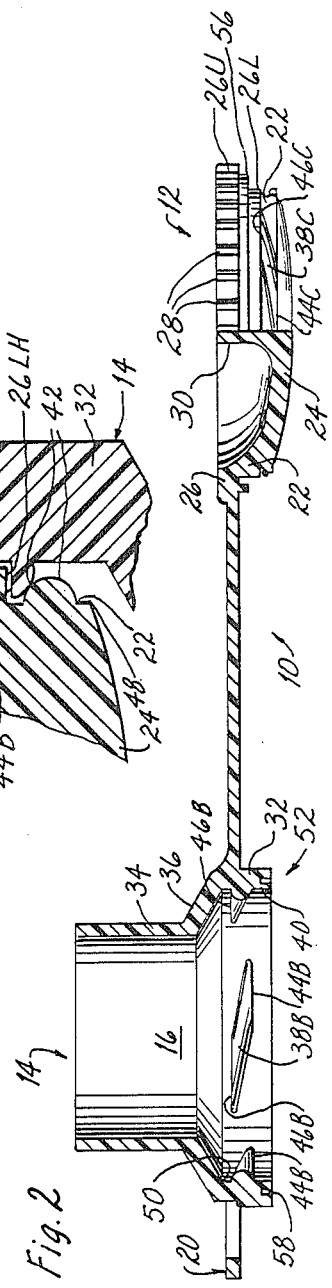
FIG. 2 is a cross sectional view of FIG. 1 along lines 2—2 illustrating the cross section configuration of the body member and the cap of the drain closure.

Referring to FIGS. 1 and 2, the drain closure valve 10 of the invention comprises a cap 12 which threadably and sealingly engages a body member 14 having an axial passageway 16 therethrough. Cap 12 may be tethered to the body member 14 by means of a tether 18. Bail, generally indicated by numeral 20, may be affixed to the opposing outside surface of the body member 14 to allLw the drain closure valve 10 and the container (not shown) to which it is connected to be suspended from a hanging device (not shown) such as a medical intravenous (IV) stand or the like. The body member 14, cap 12, and bail 20 may be integrally formed together by conventional and economical injection folding techniques.

More particularly, referring to FIG. 2, cap 12 comprises a dome-shaped configuration having upstanding annular wall portion 22 integrally formed with a bottom wall portion 24. The upstanding annular wall portion 22 further includes an annular ridge 26 formed about its upper periphery. Ridge 26 comprises a stepped configuration having an upper step portion 26U, a lower step portion 26L, an upper horizontal portion 26UH, and a lower horizontal portion 26LH (see FIG. 2A). A plurality of knurled protrusions 28 are formed on the upper step portion 26U of ridge 26 to facilitate the gripping of the cap 12 during threading or unthreading of the cap 12 from the body member 14. Further, a transverse ridge 30 is diametrically formed across the cap 12 from opposing sides of the upstanding annular wall portions 22 of the cap 20 and bottom wall portion 24 to further facilitate the theading and unthreading of the cap 12 from the body member 14.

Body member 14 comprises an upper annular wall portion 32 and a lower annular wall portion 34 of a reduced diameter joined together by a lowerly converging frustro-conical wall portion 36 difining the axial passageway 16 therethrough. The lower annular wall portion 34 of the body member 14 is particularly adaptable to be RF welded to the thin plastic sheeting of bag-type containers such as those used in the medical and other fields to form an airtight seal therewith.

Cap 12 threadably engages the body member 14 by means of a plurality of thread segments 38C and 38B integrally formed on the opstanding annular wall portion 22 of the cap 12 and the lumen 40 of the upper annular wall portion 32 of the body member 14, respectively. Each of the four illustrated mating thread segments 38C and 38B comprises a substantially semicircular cross section 42 having flat leading 44 and trailing 46 ends formed on their respective surfaces 22 and 32 at a particular pitch and lead angle. More particularly, the flat leading end 44C of the threads 38C of the cap 20 are configured to be flush with the corner 48 formed between the annular wall 22 and bottom wall 24 of the cap 12. Likewise, the flat trailing end 46C of the threads 38C of the cap 12 are formed to be flush with the ower horizontal surface 26LH of the ridge 26. Similarly, the leading end 44B of the threads 38B of the body member 14 are formed to be flush with the lower horizontal portion 26LH of the ridge 26 when the cap 12 is threaded into the body member 14. Further, the trailing end 46B of the thread 38B of the body member 14 arepositioned appreciably away from the corner 50 formed between the upper annular wall 32 and the frustro-conical wall 36 of the body member 14. Such thread configuration allows the cap 12 to be threaded into the body member 14 until the lower horizontal portion 26LH of the ridge 26 engages the upper edge 52 the upper annular wall portion 32 of the body member 14. Moreover, such thread design allows the upper edge 52 of the upper wall 32 of the body member 14 to remain appreciably close to the lower horizontal wall portion 26 of the ridge 26 during the initial unthreading of the cap 12 from the body member 14. As described hereinbelow, such feature assures that the seal formed between the cap 12 and the body member 14 will remain intact during the initial unthreading of the cap 12 from the body member 14. Thus, spellage of the fluid contained within the container from inadvertent jerking of the drain closure valve 10 during opening, is precluded.

By way of further example, the threaded engagement of the cap 12 into the body member can be illustrated with the following dimensions:

| Inner Diameter of lumen 40 = of upper wall 32 | 1.875 inch |
| --- | --- |
| Inner Diameter of annular = wall 22 of cap 12 | 1.752 inch |
| Number of mating threads = | 4 |
| Pitch diameter = | 1.815 inch |
| Pitch = | 1 inch |
| Lead angle = | 9° 56' 50" |

The sealing engagement of the cap 12 within body member 14 is accomplished by means of a partially circular protrusion 54 formed about the entire outer periphery of the lower step 26L of the ridge 26 which sealingly engages against the lumen 40 of the upper annular wall portion 32 of the body member 14 (see FIG. 2A). Indeed, such seal is formed by the circular protrusion 54 sealingly engaging against lumen 40 in such a manner that the protrusion 54 and the lumen 40 are partially deformed due to the resiliency of the material constituting the cap 12 and the body member 14.

Moreover, to prevent the lumen 40 of the upper annular wall portion 32 of the body member 14 from simply moving away from the circular protrusion 54 thereby not adequately forming a seal therewith, the cap 12 is configured to interlock with the body member 14. More particularly, such interlocking is accomplished by forming an annular tab 56 downwardly protruding rom the upper horizontal portion 26UH of the ridge 26 which engages into a corresponding annular slot 58 extending into the upper edge 52 of the upper annular wall 32 of the body member 14. Consequently, the interlocking of the downwardly protruding annular tab 56 of the cap 12 into the slot 58 of the body member 14 effectively precludes outward movement of the lumen 40 of the upper annular wall portion 32 of the body member 14 away from the circular protrusion 54. hence, an adequate seal between the lumen 40 and the protrusion 54 is assured.

The circular protrusion 54 preferably is disposed along the lower step portion 26L of the ridge 26 by a distance appreciably away from the upper horizontal portion 26UH of the ridge 26 and n line across from the downwardly extending annular tab 56. Such positioning of the circular protrusion 54 relative to the tab 56 and the upper horizontal portion 26UH of the ridge 26 assures that a seal will be formed between the lumen 40 and the protrusion 54 immediately upon the upper edge 52 of the upper wall 32 of the body member 14 engaging between the protrusion 54 and the tab 56 during threading of the cap 12 into the body member 14. Thus, such seal is formed between the cap 12 and the body member 14 before the cap 12 is tightly threaded into the body member 14 to its final closed position. Moreover, it should be appreciated that the seal between the cap 12 and body member 14 is maintained at the cap 12 is initially unthreaded from the body member 14 even when the upper edge 52 of the upper wall 32 of the body member 14 begins to move away from the upper horizontal portion 26UH of the ridge 26 of the cap 12. This feature, therefore, allows the cap 12 to be loosened from the body member 14 while maintaining a seal therewith thereby precludng spillage of the fluid from the container in the event of any jerking motion imparted to the drain closure 10 and the container during such initial unthreading. Still further, inadvertent spilling of the fluid during opening of the drain closure 10 is further minimized, if not absolutely precluded, because of the ability to maintain the upper edge 52 in close proximity or adjacent to the upper horizontal wall portion 26UH of the ridge 26 by virtue of the thread design described hereinabove.

The present disclosure includes that contained in the appended claims, as well as that of the foregoing description. Although this invention has been described in its preferred form with a certain degree of particularity, it is understood that the present disclosure of the preferred form has been made only be way of example and that numerous changes in the details of construction and the combination and arrangement of parts may be resorted to without departing from the spirit of the invention.

Now that the invention has been described,
What is claimed is:

1. A drain closure for sealing engagement with an opening in a container, comprising in combination:
 a body member having a fluid passageway therethrough, said body member further including a substantially cylindrical body annular wall portion defining a lumen and an upper edge thereof;
 a cap including a substantially cylindrical cap annular wall portion and a bottom wall portion, said cap further including a stepped annular ridge defining a ridge upper annular wall portion and a ridge lower annular wall portion joined by a ridge upper horizontal wall portion;
 means affixed to said annular wall portions of said cap and said body member for threadably engaging said cap to said body member; and
 means for sealingly engaging said cap to said body member.

2. The drain closure as set forth in claim 1, wherein said sealing means comprises a protrusion extending outwardly from said cap annular wall portion which sealingly engages said lumen of said body annular wall portion.

3. The drain closure as set forth in claim 2, wherein said cap further includes a downwardly protruding annular tab extending from said ridge upper horizontal portion for engagement with said body annular wall portion to urge said lumen into sealing engagement with said protrusion.

4. The drain closure as set forth in claim 3, wherein said annular tab engages into an annular slot formed within said upper edge of said body annular wall portion.

5. The drain closure as set forth in claim 4, wherein said thread means comprises a plurality of thread segments, semicircular in cross-section, affixed to said lumen of said body annular wall portion and said ridge lower annular portion, each said thread segments having a flat leading edge allowing said cap to threadably engage within said body member.

6. The drain closure as set forth in claim 1, wherein said ridge further includes a lower horizontal portion positioned below said ridge upper horizontal wall portion and wherein said thread means comprises a plurality of thread segments affixed to said lumen of said body annular wall portion and to said cap annular wall portion, each thread segment comprising a flat leading edge allowing said cap to be threaded into said body member with said ridge upper annular wall mating with said upper edge of said body annular wall portion and with said flat leading edge of said thread segments of said body mating against said ridge lower horizontal wall portion.

7. The drain closure as set forth in claim 6, wherein said seal means comprises an annular protrusion extending outwardly from said ridge lower annular wall portion which sealingly engages said lumen of said body annular wall portion.

8. The drain closure as set forth in claim 7, wherein said cap further includes a downwardly protruding annular tab which urges said lumen in sealing engagement with said protrusion.

9. The drain closure as set forth in claim 8, wherein said downwardly protruding annular tab engages within an annular slot formed within said upper edge of said body annular wall portion.

10. The drain closure as set forth in claim 1, wherein said ridge upper annular wall portion includes knurled protrusions about the periphery thereof.

11. The drain closure as set forth in claim 1, wherein said cap is tethered to said body member.

12. The drain closure as set forth in claim 1, wherein said body member further comprises a bail.

* * * * *

UNITED STATES PATENT AND TRADEMARK OFFICE
CERTIFICATE OF CORRECTION

PATENT NO. : 4,754,895

DATED : July 5, 1988

INVENTOR(S) : George E. Lardner and Jacek Weinheimer

It is certified that error appears in the above—identified patent and that said Letters Patent is hereby corrected as shown below:

in column 1, line 42, please delete "aforementioped" and insert therefor -- aforementioned --.

in column 3, at line 16, please delete "he" and insert therefor -- the --.

in column 4, at line 3, please delete "folding" and insert therefor -- molding --.

in column 4, at line 26, please delete "difining" and insert therefor -- defining --.

in column 4, at line 34, please delete "opstanding" and insert therefor -- upstanding --.

in column 4, at line 46, please delete "ower" and insert therefor -- lower --.

in column 4, at line 53, please delete "arepositioned" and insert therefor -- are positioned --.

in column 4, at line 68, please delete "spellage" and insert therefor -- spillage --.

in column 5, at line 32, please delete "rom" and insert therefor -- from --.

in column 5, at line 46 please delete "n" and insert therefor -- in --.

UNITED STATES PATENT AND TRADEMARK OFFICE
CERTIFICATE OF CORRECTION

PATENT NO. : 4,754,895

DATED : July 5, 1988

INVENTOR(S) : George E. Lardner and Jacek Weinheimer

It is certified that error appears in the above-identified patent and that said Letters Patent is hereby corrected as shown below:

in column 3, at line 66, please delete "allLw" and insert therefor

-- allow --.

Signed and Sealed this

Third Day of January, 1989

Attest:

DONALD J. QUIGG

Attesting Officer

Commissioner of Patents and Trademarks